Aug. 18, 1970 L. R. B. HERVEY ETAL Re. 26,939

METHOD FOR IMPROVING A FLUFFED FIBROUS WOOD PULP BATT FOR USE IN SANITARY PRODUCTS AND THE PRODUCTS THEREOF

Original Filed Nov. 9. 1966

INVENTORS:

LAURENCE R. B. HERVEY and DONALD K. GEORGE

BY Barrett, Bell, Seltzer, Beck + Arend

ATTORNEYS

United States Patent Office

Re. 26,939
Patented Aug. 18, 1970

26,939

METHOD FOR IMPROVING A FLUFFED FIBROUS WOOD PULP BATT FOR USE IN SANITARY PRODUCTS AND THE PRODUCTS THEREOF

Laurence R. B. Hervey, West Concord, Mass., and Donald K. George, Greenwood, S.C., assignors, by direct and mesne assignments, to Riegel Textile Corporation, New York, N.Y., a corporation of Delaware Original No. 3,395,708, dated Aug. 6, 1968, Ser. No. 593,004, Nov. 9, 1966. Application for reissue Oct. 8, 1969, Ser. No. 866,117

Int. Cl. A61f *13/16*

U.S. Cl. 128—284 7 Claims

Matter enclosed in heavy brackets [ ] appears in the original patent but forms no part of this reissue specification; matter printed in italics indicates the additions made by reissue.

ABSTRACT OF THE DISCLOSURE

A method for improving a fluffed fibrous wood pulp batt and the resulting product thereof comprising impregnating a wet slurry of wood pulp with a cationic debonding agent, forming the wet slurry into a wet pressed wood pulp sheet, drying, mechanically fiberizing the sheet and air-laying the fibers to form a fluffed fibrous wood pulp batt. This method and improved product provides a fluffed fibrous wood pulp batt which is substantially completely fiberized to eliminate undesirable residual sheet particles and minimize fiber breakage and dust to provide longer, stronger and more uniform fibers for producing greater loft, moisture absorption and strength in the batt to adapt the same for use in sanitary products or the like.

This invention relates to a lovel method for improving a fluffed fibrous wood pulp batt wherein the fluffed fibrous wood pulp is substantially completely fiberized to eliminate undesirable residual unfiberized sheet particles and minimize fiber breakage and dust so as to provide longer, stronger and more uniform fibers for producing greater loft, moisture absorption and strength in the batt. Additionally, the invention relates to the utilization of the improved fluffed fibrous wood pulp batt in the construction of diapers, sanitary napkins, bandages, nursing pads, etc., which are collectively designated hereinafter as "sanitary products."

Conventionally, fluffed fibrous wood pulp batts for use in sanitary products or the like have been formed by mechanically fiberizing a dried wet pressed wood pulp sheet with a hammermill or other suitable mechanical means and forming the resulting fibers into a coherent web or batt with an air-laying device. Due to the difficulty of mechanically fiberizing the pulp sheet, these prior fiberizing operations were dusty and necessarily utilized a large energy requirement. The resulting fiberized fluffed wood pulp batt had the undesirable characteristics of not being fully fiberized resulting in non-unformity of fiber lengths, fiber breakage, residual sheet particles, etc. which reduced loft, moisture absorption and strength in the batt. Batts formed by these conventional methods often had a rough granular texture and did not provide maximum comfort to the wearer when used in sanitary products worn against the body to absorb body fluids.

The novel method of the present invention overcomes the above problems and, therefore, provides an improved fluffed wood pulp batt and resulting improved sanitary products utilizing the improved fluffed wood pulp batt.

Some of the features of this invention having been stated, other features will appear as the description proceeds, when taken in conjunction with the accompanying drawings, in which—

Figure 1:
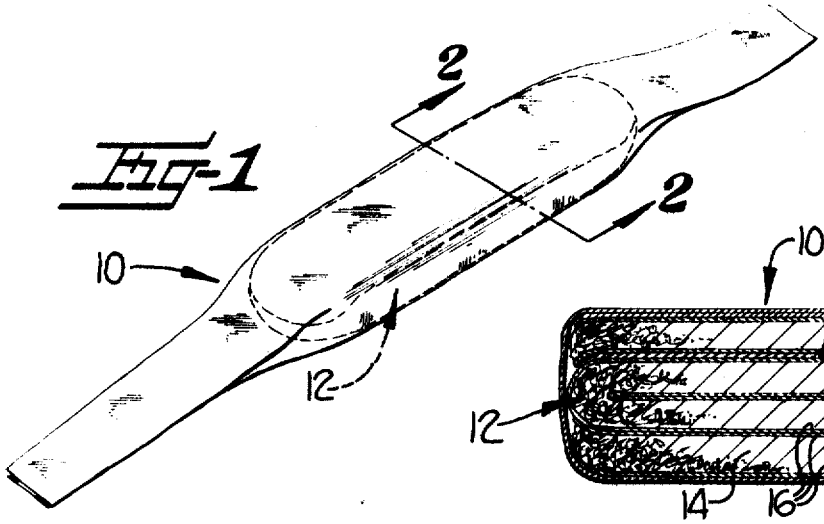
FIGURE 1 is a reduced perspective view of a sanitary napkin utilizing the improved fluffed fibrous wood pulp batt of this invention.

In accordance with the present invention, it has been discovered that a fluffed fibrous wood pulp batt, adapted for use in sanitary products or the like, may be improved by being substantially completely fiberized so as to eliminate undesirable residual sheet particles and minimize fiber breakage and dust providing longer, stronger and more uniform fibers for producing greater loft, softness, moisture absorption and strength in the batt. The improvement is accomplished by impregnating a wet slurry of wood pulp with a cationic debonding agent, forming the wet slurry into a wet pressed wood pulp sheet, and mechanically fiberizing the dried sheet to form a substantially completely fiberized fluffed fibrous wood pulp batt.

Conventionally, wet pressed wood pulp sheets are formed by the utilization of a pulping operation which reduces wood into pulp and forms a wet slurry of wood pulp. From the pulping process, the wet slurry of wood pulp is led to a conventional paper machine or other suitable apparatus and formed into a sheet which is then wet pressed and dried. The above operations are conventional and well known to those with ordinary skill in the art and, therefore, further details herein are deemed unnecessary.

By this invention, it has been found most advantageous to add the cationic debonding agent to the wet slurry of wood pulp following the pulping operation, preferably in a stock chest or other suitable storage means prior to the papermaking process. It has been found preferable to allow the cationic debonding agent to remain in the wet slurry of unfiberized wood pulp for at least approximately ten minutes before forming the wet pressed wood pulp sheet on the paper machine. The cationic debonding agent, due to the positive charge thereof, is attracted to the wood pulp and substantially absorbed onto it and weakens the inherent bonding characteristics of the wood pulp during the formation of the wet pressed wood pulp sheet on the paper machine. Manifestly, this action will allow the wood pulp sheet to be more easily mechanically fiberized for forming a substantially completely fiberized, fluffed, wood pulp batt resulting in the above-described improved qualities of the fiberized, fluffed, wood pulp matt.

Suitable cationic debonding agents for accomplishing the above-described purposes of the present invention fall within the class of long chain cationic surfactants, preferably with at least twelve carbon atoms in at least one alkyl chain, and illustrative, but non-limiting, specific examples of same are fatty dialkyl amine quaternary salts, mono fatty alkyl tertiary amine salts, primary amine salts, and unsaturated fatty alkyl amine salts.

The amount of debonding agent to be added to the wet slurry of wood pulp may vary substantially, but in actual practice it has been found that amounts of about 0.1% to 5.0%, based on the weight of dry wood pulp, may be used. Amounts less than 0.1% provide very little improvement in the fiberization process. A typical treatment which has been found to give very good results is 1.5% of di hydrogenated tallow dimethyl ammonium chloride or 1.0% of di-soya dimethyl ammonium chloride.

The improved fluffed fibrous wood pulp batt, produced in accordance with the present invention, is particularly adaptable for use in the manufacture of sanitary products, above described, or for other similar products which require an interior pad of dispersible fibrous absorbent material adapted to absorb the body fluids of the wearer.

An interior pad formed from the improved fluffed fibrous wood pulp batt of this invention is particularly desirable for use with a flushable paper wrapper or cover material of the type disclosed is copending application Ser. No. 572,929, now U.S. Patent No. 3,370,590, issued Feb. 27, 1968, assigned to the same assignee as the present invention, for producing a completely flushable sanitary product.

Referring now to the drawings, two examples of commerical sanitary products are shown therein and will be specifically described hereinafter; however, it is pointed out that other commercial sanitary products may be produced.

Figure 2:
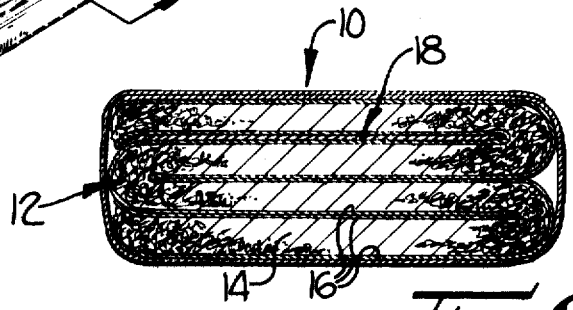
FIGURE 2 is a full scale cross-sectional view of the sanitary napkin of FIGURE 1 taken substantially along the line 2—2 of FIGURE 1.

Referring now to FIGURES 1 and 2, a sanitary napkin may be formed which comprises a wraper or cover layer 10 for completely enclosing a layered, folded or otherwise formed pad 12 utilizing the improved fluffed fibrous wood pulp batt 14 of the present invention. The wrapper or cover material 10 may be woven gauze or other conventional materials or it may be formed of the flushable paper described in the above-mentioned copending application. This wrapper or cover material will be manufactured in the usual configuration and secured around the interior pad 12 to form attachment tabs on either side of the interior pad for attachment to the normal belt or holding means when utilized by the wearer.

In one commercially advantageous form, the interior pad 12 is formed from a cut fluffed fibrous wood pulp batt 14 having a cut layer of creped cellulose wadding 16 superimposed thereon. The batt 14 and the creped cellulose wadding layer 16 are then folded with multiple reperse folds extending in the longitudinal direction of the pad to form a multi-layer interior pad 12, as shown in FIGURE 2. The interior pad 12 may also include a conventional moisture barrier 18 formed of any suitable liquid impervious material.

Figure 3:
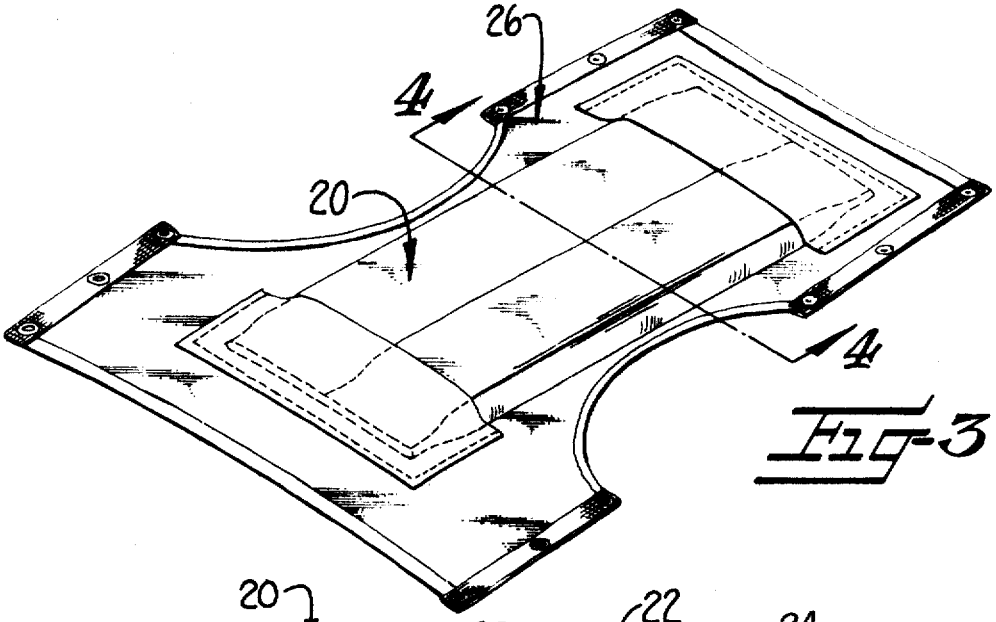
FIGURE 3 is a reduced perspective view of a diaper pad utilizing the improved fluffed fibrous wood pulp batt of this invention and illustrated as being held in a holder for application to a baby.
Figure 4:
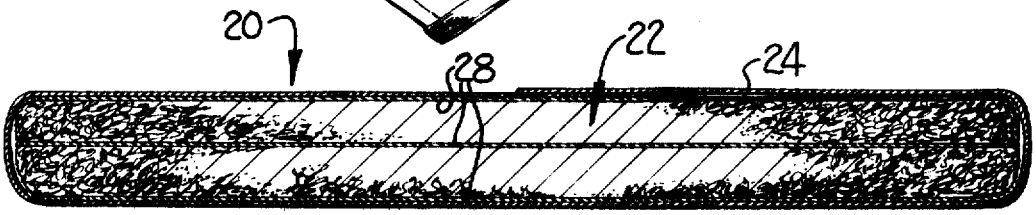
FIGURE 4 is a full scale cross-sectional view of the diaper pad of FIGURE 3 taken substantially along the line 4—4 of FIGURE 3.

Referring to FIGURES 3 and 4, a diaper pad may be formed which comprises a wrapper or cover layer 20 for completely enclosing a layered, folded or otherwise formed interior pad 22 utilizing the improved fluffed fibrous wood pulp batt 24 formed according to this invention.

The wrapper or cover material 20 may be woven gauze or other conventional materials or it may be formed of the flushable paper described in the above-mentioned copending application. This wrapper or cover material is formed in a generally rectangular configuration and is secured around the generally rectangular interior pad 22 for use as a diaper pad to be inserted within a holder 26 for placing in position on the body of the wearer.

In one commercially advantageous form, the interior pad 22 utilizes two cut layers of fluffed fibrous wood pulp 24 superimposed on each other and having layers of creped cellulose wadding 28 superimposed therebetween and on each of the outside surfaces thereof.

Various modifications and changes may be effected in the foregoing description without departing from the scope of this invention as defined in the appended claims.

What is claimed is:

1. Method for improving a fluffed fibrous wood pulp batt adapted for use in sanitary products or the like wherein the fluffed fibrous wood pulp is substantially completely fiberized to eliminate undesirable residual sheet particles and minimize fiber breakage and dust so as to provide longer, stronger and more uniform fibers for producing greater loft, moisture absorption and strength in said batt, said method comprising impregnating a wet slurry of wood pulp with a cationic debonding agent, forming said wet slurry into a wet pressed wood pulp sheet, drying, mechanically fiberizing said sheet and airlaying said fibers to form a fluffed wood pulp batt.

2. A method, as defined in claim 1, in which the cationic debonding agent is a long chain cationic surfactant with at least 12 carbon atoms in at least one alkyl chain.

3. A method, as defined in claim 1, in which said debonding agent is selected from the group consisting of fatty dialkyl quaternary amine salts, mono fatty alkyl tertiary amine salts, primary amine salts, and unsaturated fatty alkyl amine salts.

4. A method, as set forth in claim 1, in which from about 0.1% to 5.0% of said debonding agent based on fiber content is impregnated in the wet slurry of wood pulp.

5. An improped fluffed fibrous wood pulp batt adapted for use in sanitary products or the like produced in accordance with the method of claim 1.

*6. Method for rendering a fibrious wood pulp sheet easily fiberizable comprising partially debonding the normally self-bonding fibers of the sheet by impregnating a wet slurry of wood pulp with about 0.5% to 1.5 of a cationic debonding agent which is a long chain cationic surfactant having at least 12 carbon atoms in at least one alkyl chain, forming said wet slurry into a fiberizable wet pressed wood pulp sheet and drying said pulp sheet.*

*7. A fiberizable wood pulp sheet comprising normally self-bonding fiber partially debonded throughout the sheet to enable fiberizing of the sheet into a lofty fluffy fibrous material, said sheet being impregnated throughout with approximately 0.5% to 1.5% of a long chain cationic surfactant having at least 12 carbon atoms in at least one alkyl chain for effecting the partial debonding and for rendering said sheet easily fiberizble.*

References Cited

The following references, cited by the Examiner, are of record in the patented file of this patent or the original patent.

UNITED STATES PATENTS

| | | | |
|---|---|---|---|
| 2,600,882 | 6/1952 | Kellett et al. | 128—290 |
| 1,907,046 | 5/1933 | Darrah | 162—213 |
| 2,618,816 | 11/1952 | Joa | 128—290 |
| 2,634,229 | 4/1953 | De Wet | 128—284 |
| 2,940,890 | 6/1960 | Brown | 162—179 |
| 2,945,863 | 7/1960 | Buc et al. | 162—179 |

FOREIGN PATENTS

| | | |
|---|---|---|
| 223,779 | 5/1958 | Australia. |
| 983,367 | 2/1965 | Great Britain. |

CHARLES F. ROSENBAUM, Primary Examiner

U.S. Cl. X.R.

162—166

UNITED STATES PATENT OFFICE

CERTIFICATE OF CORRECTION

Patent No. RE 26,939 Dated August 18, 1970

Inventor(s) Laurence R. B. Hervey and Donald K. George

It is certified that error appears in the above-identified patent and that said Letters Patent are hereby corrected as shown below:

Column 1, line 36, "lovel" should be --novel--. Column 2, line 54, "matt" should be --batt--. Column 3, line 21 "wraper" should be --wrapper--, Column 3, line 38, "reperse" should be --reverse--. Column 4, line 25 (Claim 5), "improped" should be --improved--, Column 4, line 31 (Claim 6), "1.5" should be --1.5%--. In the References, line 56, "Brown" should be --Braun--.

SIGNED AND SEALED NOV 10 1970

(SEAL)
Attest:

Edward M. Fletcher, Jr.
Attesting Officer

WILLIAM E. SCHUYLER, JR.
Commissioner of Patents